United States Patent
Beaty et al.

(10) Patent No.: US 10,028,729 B2
(45) Date of Patent: Jul. 24, 2018

(54) SYSTEM AND METHOD FOR TESTING OPERABILITY OF A LENS AND SELECTED TRANSDUCER ELEMENTS OF AN ACOUSTIC PROBE

(71) Applicant: General Electric Company, Schenectady, NY (US)

(72) Inventors: Gregory Alan Beaty, Boulder, CO (US); James Ginther, Boulder, CO (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 901 days.

(21) Appl. No.: 14/535,638

(22) Filed: Nov. 7, 2014

(65) Prior Publication Data
US 2016/0131746 A1    May 12, 2016

(51) Int. Cl.
| | |
|---|---|
| G01S 15/00 | (2006.01) |
| A61B 8/00 | (2006.01) |
| G01S 7/52 | (2006.01) |
| G01S 15/89 | (2006.01) |

(52) U.S. Cl.
CPC .............. *A61B 8/58* (2013.01); *G01S 7/5205* (2013.01); *G01S 15/8915* (2013.01); *A61B 8/54* (2013.01)

(58) Field of Classification Search
USPC ........................................................ 367/137
See application file for complete search history.

(56) References Cited

U.S. PATENT DOCUMENTS

| | | |
|---|---|---|
| 5,517,994 A | 5/1996 | Burke et al. |
| 6,920,776 B2 | 7/2005 | Gessert et al. |
| 6,928,856 B2 | 8/2005 | Gessert et al. |
| 7,007,539 B2 | 3/2006 | Gessert et al. |
| 7,028,529 B2 | 4/2006 | Gessert et al. |
| 7,155,957 B2 | 1/2007 | Gessert et al. |
| 7,246,264 B2 | 7/2007 | Grellmann et al. |
| 7,266,987 B2 | 9/2007 | McCartan et al. |
| 7,272,762 B2 | 9/2007 | Horwath et al. |
| 7,278,289 B2 | 10/2007 | Gessert et al. |
| 7,726,172 B2 | 6/2010 | Moore et al. |

(Continued)

OTHER PUBLICATIONS

International Search Report and Written Opinion for International Application No. PCT/US2015/042671 dated Oct. 29, 2015. 8 pages.

(Continued)

*Primary Examiner* — James R Hulka

(57) ABSTRACT

A system and method for testing an acoustic probe is provided. The system includes an electric signal generator connected to transmit an electric generator signal into selected transducer elements of the acoustic probe. The selected of transducer elements of the acoustic probe convert the electrical signal into an acoustic signal that reflects off the lens of the acoustic probe and is then converted by the selected transducer elements of the acoustic probe into a reflected electrical signal. An analysis engine is connected to receive the reflected electrical signal and determine the operability of lens and each selected transducer element for acoustic and electrical conversion. A display provides an illustration indicative of the operative ability of the lens and the selected transducer element of the acoustic probe for acoustic and electrical conversion.

16 Claims, 3 Drawing Sheets

(56) References Cited

U.S. PATENT DOCUMENTS

| | | | |
|---|---|---|---|
| 7,880,488 B2 | 2/2011 | Dananay et al. | |
| 8,008,906 B2 | 8/2011 | Valenti, III | |
| 8,159,900 B2 | 4/2012 | Moore et al. | |
| 8,164,976 B2 | 4/2012 | Moore et al. | |
| 8,169,853 B2 | 5/2012 | Moore et al. | |
| 8,199,920 B2 | 6/2012 | Valenti, III | |
| 8,215,152 B2 | 7/2012 | Kim | |
| 8,893,541 B2 | 11/2014 | Gessert et al. | |
| 2004/0153862 A1* | 8/2004 | Grellnnann | A61B 8/00 714/43 |
| 2004/0211239 A1* | 10/2004 | Gessert | G01N 29/30 73/1.82 |
| 2004/0211240 A1* | 10/2004 | Gessert | G01N 29/2487 73/1.82 |
| 2004/0213417 A1* | 10/2004 | Gessert | H04R 29/002 381/66 |
| 2005/0072207 A1* | 4/2005 | Gessert | G01N 29/30 73/1.82 |
| 2005/0092059 A1* | 5/2005 | Gessert | G01N 29/30 73/1.82 |
| 2006/0101896 A1* | 5/2006 | Gessert | G01N 29/2487 73/1.82 |
| 2006/0191315 A1* | 8/2006 | McCartan | G01N 29/30 73/1.82 |
| 2007/0011528 A1* | 1/2007 | Horwath | G01R 31/2815 714/727 |
| 2007/0234807 A1* | 10/2007 | Moore | G01H 3/12 73/570 |
| 2010/0109694 A1* | 5/2010 | Dananay | H01R 27/00 324/756.05 |
| 2010/0122566 A1* | 5/2010 | Kim | A61B 8/00 73/1.82 |
| 2010/0150358 A1* | 6/2010 | Valenti | H04R 29/00 381/58 |
| 2010/0194377 A1* | 8/2010 | Valenti, III | G01R 13/0272 324/76.38 |
| 2011/0030448 A1* | 2/2011 | Moore | G01N 29/30 73/1.82 |
| 2011/0032793 A1* | 2/2011 | Moore | H04R 29/00 367/13 |
| 2011/0032799 A1* | 2/2011 | Moore | G01S 7/52052 367/95 |
| 2014/0020469 A1* | 1/2014 | Gessert | G10K 11/341 73/618 |

OTHER PUBLICATIONS

International Application PCT/US2015/042671, filed Jul. 29, 2015.
International Search Report and Written Opinion for International Application No. PCT/US2015/042671, dated Oct. 29, 2015, 8 pages.

\* cited by examiner

SYSTEM AND METHOD FOR TESTING OPERABILITY OF A LENS AND SELECTED TRANSDUCER ELEMENTS OF AN ACOUSTIC PROBE

TECHNICAL FIELD

The subject herein generally relates to a system and method to test an acoustic probe, and more specifically to a system and method to test operability of selected transducer elements and the lens of the acoustic probe to perform between acoustic and electrical conversion.

BACKGROUND

The statements in this section merely provide background information related to the disclosure and may not constitute prior art.

Acoustic imaging techniques have been found to be valuable in a variety of applications. A certain acoustic imaging technique referred to as ultrasound imaging is perhaps the most well-known, but acoustic techniques are more generally used at a variety of different acoustic frequencies for imaging a variety of different phenomena. Certain acoustic imaging techniques use transmission and detection of acoustic radiation in identification of structural defects, detection of impurities, as well as detection of tissue abnormalities in living bodies. All such acoustic imaging techniques rely generally on the fact that different structures, whether they are abnormal bodily tissues or defects in an airplane wing, have different impedances to acoustic radiation. Certain known acoustic imaging systems include an acoustic probe having multiple transducer elements that may have linear, curved-linear, phased-array, or similar characteristics to control the transmission and detection of acoustic radiation. Degradation in performance of such transducer elements is known to occur with extended transducer use and/or through user abuse. Certain known techniques to test the degradation of the transducer elements require the use of a reflective target and a tank of water as a conductive medium in order to analyze the performance of such transducer elements. A drawback of such acoustic testing techniques includes the difficulty in alignment of the acoustic probe with respect to the water tank and target, such difficulty encumbering the speed and repeatability of the acoustic test.

There is, therefore, a general need in the art for a system and method of testing acoustic probes that does not require certain cumbersome infrastructure (i.e., target and water tank) and yet improves speed and repeatability of the test of the operability of the acoustic probe.

BRIEF SUMMARY

In view of the above concerns associated with use of acoustic testing techniques, there is a need for systems, methods and computer program products that provides for a quick and repeatable test of the operative ability of the acoustic probe that does not require use of certain cumbersome infrastructure such as an acoustic target or a water tank as a conductive medium. The above-described needs are addressed by the embodiments of the subject matter described herein.

The subject matter described herein includes a system for testing an acoustic probe having a lens in combination with a plurality of transducing elements adapted to convert between acoustic and electrical signals, the system comprising: an electric signal generator connected to transmit an electric generator signal into the plurality of transducer elements of the acoustic probe, wherein the plurality of transducer elements of the acoustic probe converts the electrical signal into an acoustic signal that reflects off the lens of the acoustic probe and is then converted by the transducer elements of the acoustic probe into a reflected electrical signal; an analysis engine connected to receive the reflected electrical signal and determine operability of lens and each selected transducer element for acoustic and electrical conversion; a display configured to provide an illustration indicative of the operative ability of the lens and the selected transducer element of the acoustic probe for acoustic and electrical conversion.

According to another aspect, a method of testing an acoustic probe having a plurality of transducing elements adapted for conversion between acoustic and electrical signals is provided. The method comprises the steps of: sending an electrical generator signal from an electric signal generator into at least one of the selected transducer elements of the acoustic probe; detecting a reflected electrical signal from the selected transducer elements of the acoustic probe generated in converting an acoustic signal transmitted from the transducer elements of the acoustic probe and reflected off the lens of the acoustic probe back toward the transducer elements of the acoustic probe; and displaying an indication of the operative ability of the lens and the selected transducer element of the acoustic probe for acoustic and electrical conversion.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. The term user and/or the plural form of this term is used to generally refer to those persons capable of accessing, using, or benefiting from the present disclosure. As used herein, when the phrase "at least" is used, it is open-ended in the same manner as the term "comprising" is open-ended.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
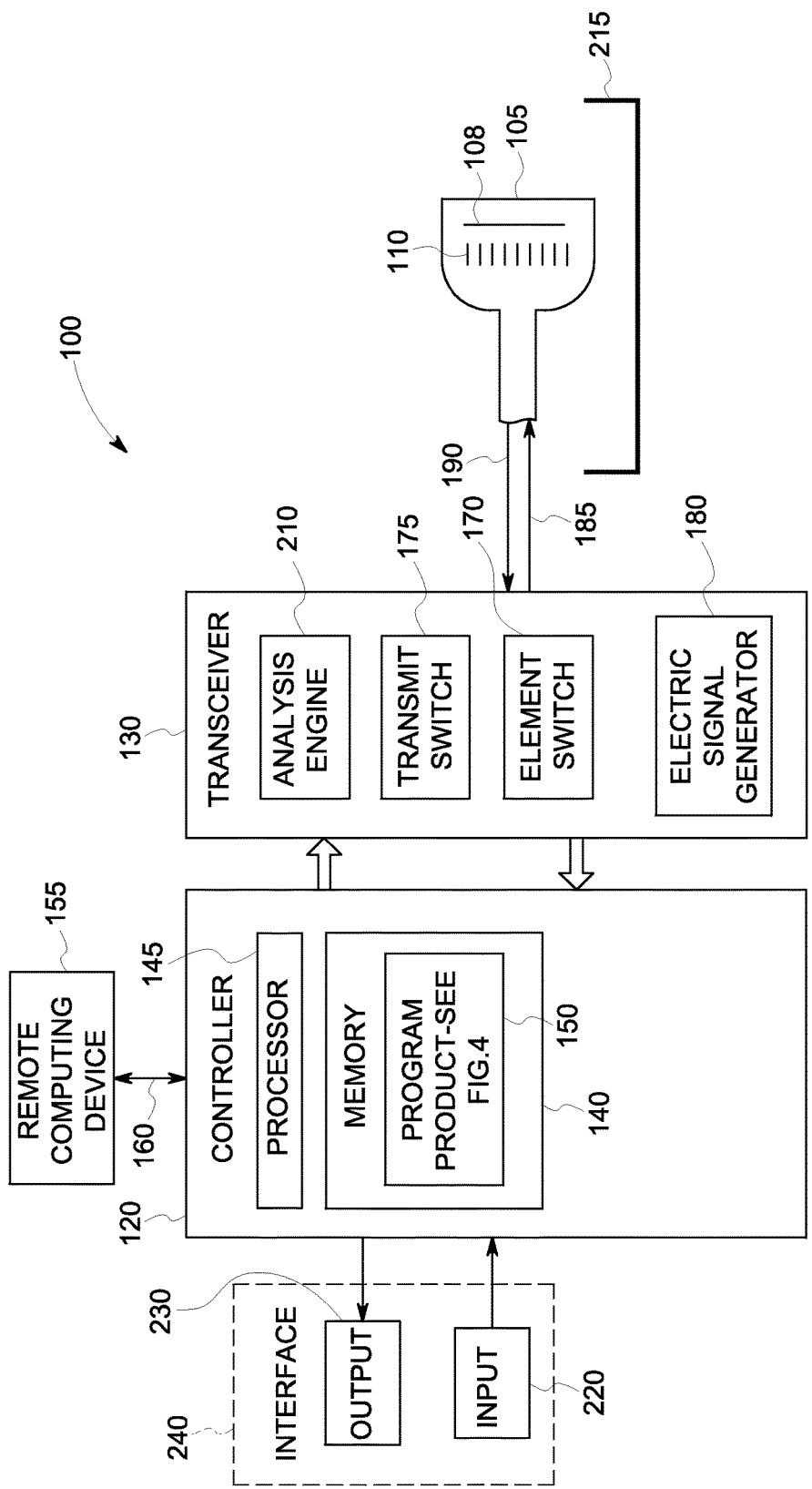
FIG. 1 shows a schematic block diagram of an example of a system in accordance to the subject matter described herein.

FIG. 1 illustrates one embodiment of a system 100 for testing an operability of an acoustic probe 105 having a lens 108 and a series of transducer elements (shown schematically by lines) 110 adapted to convert between acoustic and electrical signals. In general, the system 100 comprises a controller 120 connected to communicate with a transceiver 130 in testing of the operability of the acoustic probe 105. Each transducer element 110 of the acoustic probe 105 generally includes a piezoelectric crystal (not shown) constructed to convert between acoustic and electrical signals, backing material (not shown), matching layers (not shown), and a lens 108 to focus the generated acoustic energy in measurement of an impedance of structures (e.g., bodily tissue, etc.). In particular, the piezoelectric crystals are known in the art to convert received electric signals to acoustic radiation or signals for emission, as well as to convert incident acoustic radiation back to electrical signals for translation into images indicative of the material of the incident structure.

The controller 120 of the system 100 is generally operative to receive, process, and convey information to and from the electrical signal generator and the transceiver 130. The example of the controller 120 can generally include a memory 140 having a series of computer readable program instructions for execution by a computer or hardware processor (herein "computer processor") 145. The example memory 140 can include or be a non-transitory, tangible, computer program product 150 of varying type generally operable to store electronic formatted data or information and program instructions accessible and readable by the computer processor 145. In certain examples, the memory 140 can be accessible by a remote computing device 155 via a network connection 160.

The computer-readable instructions can comprise a programming code for execution by the computer processor 145. The programming code can be embodied in software stored on the memory 140 independent of or in combination with software embodied in firmware or dedicated hardware. The computer program product 150 can include a computer-readable storage medium that is tangible, non-transitory, and having volatile and non-volatile, and removable and non-removable media for storage of electronic-formatted information such as the computer readable program instructions or modules of instructions, data, etc. that may be stand-alone or as part of the controller 120. As used herein, the term tangible, non-transitory computer readable storage medium can be expressly defined to include any type of computer readable storage device and/or storage disk and to exclude propagating signal media and to exclude transmission media. As used herein, "non-transitory computer readable storage medium" and "non-transitory machine readable storage medium" can be used interchangeably.

Examples of the memory 140 can include, but are not limited to, random access memory (RAM), read only memory (ROM), Synchronous Dynamic Random Access Memory (SDRAM), Dynamic Random Access Memory (DRAM), EEPROM, flash memory, a cache, compact disc (CD), digital versatile disc (DVD) or other optical storage, magnetic cassettes, magnetic tape, magnetic disk storage or other magnetic storage devices, a hard drive, a flash memory, or any other medium which can be used to store the desired electronic format of information or program instructions for a duration and which can be accessed by the computer processor 145 or at least a portion of the controller 120.

The example computer processor 145 can include hardware to execute one or more tasks as defined by the computer readable program instructions. The computer processor 145 can be, for example, part of a computer server, a laptop or desktop, a mobile device (e.g., a cell phone, a smart phone, a tablet such as an IPAD™), a personal digital assistant (PDA), an Internet appliance, or any other type of known computing device. For example, the computer processor 145 can be implemented by one or more integrated circuits, logic circuits, microprocessors or controllers from any desired family or manufacturer.

The memory 140 and computer processor 145 as referred to herein can be stand-alone or integrally constructed as part of various programmable computing devices of various types, including for example a cache, a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like and any combination thereof operable to execute the instructions associated with implementing the method (discussed later) of the subject matter described herein.

The transceiver 130 connects to the acoustic probe 105 for testing. An example of the transceiver 130 can include a transducer element selector or element switch 170, a transmit selector switch 175, and an electrical signal generator 180. The transducer element selector switch 170 can direct signal transmissions or communications to and from the one or more selected transducer elements 110 of the series of transducer elements 110 in the acoustic probe 105 being tested. An example of the transducer element selector switch 170 can be a relay matrix configured to establish connections in a desired sequential manner with the plurality of transducer elements 110 of the acoustic probe 105, either individually or in groups, that permits selective evaluation of individual or multiple transducer elements 110 of the acoustic probe 105. The relay matrix can comprise a bidirectional switching array capable of establishing the desired connections. The electrical characteristics of the relay matrix can be configured not to impact the evaluation of the transducer elements 110 of the acoustic probe 105. For example, the transducer element selector switch 170 can include an array of miniature relays, or a semiconductor-based switching integrated circuitry. In regard to the array of relays, the array of relays may be arranged in groups and in various circuit topologies to enhance transmission of the electrical generator signals and/or reflected electrical signal.

The transmit switch 175 in a first position can direct an electrical generator signal 185 from the electrical signal generator 180 to the selected transducer elements 110 of the acoustic probe 105, and in a second position can direct receipt of transmission of a reflected electrical signal (described below) 190 from the acoustic probe 105. The electrical signal generator 180 generates and transmits the electrical generator signal 185 to the selected transducer elements 110 of the acoustic probe 105 for testing. The electrical signal generator 180 can be at a predefined or input instructed frequency or amplitude so as to trigger the selected transducer element 110 to convert the electrical generator signal to an acoustic signal at a desired frequency. An example of the electrical signal generator 180 can be an alternating voltage source operable to generate an analog or digital signal in a radio frequency (RF) range.

In response to receipt of the transmitted electrical generator signal 185, properly operative or functioning selected transducer elements 110 respond with conversion of the electrical generator signal 185 to an acoustic signal for transmission through the lens 108. In particular with respect to transducer elements 110 that comprise piezoelectric elements, transducer elements 110 impacted by receipt of the electrical generator signal 185 (e.g., variable voltage signal) in accordance to the piezoelectric effect. Due to the open air interface, the lens can reflect at least a certain portion of the converted acoustic energy or radiation back toward the selected transducer elements 110. In accordance to the piezoelectric effect, the selected transducer elements can re-convert the acoustic energy back into the reflected electrical signal 190. The transmit switch 175 of the transceiver 130 is connected to route or direct this reflected electrical signal 190 from the selected transducer elements 110 to the analysis engine 210 for analysis to determine the operability or functionality of the lens and selected transducer elements 110.

The transceiver 130 can include an analysis engine 210 configured to detect receipt of and analyze the reflected electrical signal from the selected transducer element. In one example, the analysis engine 210 can be configured to communicate raw data from the reflected electrical signal for visualization to the user. In another example, the analysis engine 210 can include a computational circuitry configured to compare predefined parameters of the received electrical transducer signal from the selected transducer element relative to a threshold. Examples of the parameters can include amplitude, frequency, etc. of the signal. Examples of the threshold can be predefined or based on benchmark values from measurements from other transducer elements 110 of the acoustic probe 105 being tested. The analysis engine 210 can further include an amplifier, an analog-to-digital converter, etc. to filter and process the electrical transducer signal for analysis. In one example, the analysis engine 210 can be provided by a personal computer, smartphone, tablet, a mainframe, or a laptop, whose mobility makes it especially convenient. Although FIG. 1 shows the analysis engine 210 as integrated with transceiver 130, the analysis engine 210 can include computer program instructions or circuitry or combination thereof as part of the controller 120 or transceiver 130 or remote computing device or combination thereof.

The controller 120 of the system 100 can also be configured to communicate instructions to and from the remote computer devices 155. Examples of remote computer devices 155 as referenced herein can include: a mobile telephone; a computer such as a desktop or laptop type; a Personal Digital Assistant (PDA) or mobile phone; a notebook, tablet or other mobile computing device; or the like and any combination thereof. The subject matter of this description may be implemented as a stand-alone computer program product or as an application configured for execution by one or more of the remote computing devices 155. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the remote computing device(s) 155.

The network 160 can facilitate transmission of electronic or digital data to and from the system 100 with respect to the remote computer devices 155. The example network 160 can be a wired interface (e.g., a data bus, a Universal Serial Bus (USB 2.0 or 3.0) connection, etc.) and/or a wireless interface (e.g., radio frequency, infrared, optical, near field communication (NFC), etc.), a wide area network (WAN); a local area network (LAN); the Internet; a cloud-based computing infrastructure of computers, routers, servers, gateways, etc.; or any combination thereof associated therewith that allows the system 100 or portion thereof to communicate with various computing devices 155 described above. With respect to the example of the network 160 as including a cloud-based infrastructure, the system 100 can share information via web-based applications, cloud storage and cloud services. For example, a Web-based portal may be used to facilitate access to information, etc. The system 100 can illustrate the Web-based portal as a central interface to access information and applications, and data may be viewed through the Web-based portal or viewer, for example. Additionally, data may be manipulated and propagated using the Web-based portal, for example. The Web-based portal can be accessible locally (e.g., in an office) and/or remotely (e.g., via the Internet and/or other network or connection 160), for example.

The controller 120 can also be in communication with an input or input device 220 and an output or output device 230. Examples of the input device 220 include a keyboard, joystick, mouse device, touch-screen, pedal assemblies, track ball, light wand, voice control, or similar known input device known in the art. Examples of the output device 230 include a liquid-crystal monitor, a plasma screen, a cathode ray tube monitor, a touch-screen, a printer, audible devices, etc. The input device 220 and output device 230 can be independent of one another, or combination as an interface 240 to the system 100.

Having provided an example of one construction of the system 100 as shown in FIG. 1 in accordance with above-description, the following is a description of an example of a method 300 (See FIG. 2) to operate the system 100 in accordance with the subject matter described herein. It should also be understood that the sequence of the acts or steps of the method 300 as discussed in the foregoing description can vary. Also, it should be understood that the method 300 may not require each act or step in the foregoing description, or may include additional acts or steps not disclosed herein. It should also be understood that one or more of the steps of the method 300 can be represented by one or more computer program modules of computer-readable program instructions stored in the memory 140 of the system 100. As mentioned above, the method 300 can be implemented using coded instructions (e.g., computer and/or machine readable instructions). The terms module and component as referenced herein can generally represent program code or instructions that causes specified tasks when executed on the computer processor 145. The program code can be stored in one or more computer readable mediums that comprise the memory 140 and computer program product 150.

Figure 2:
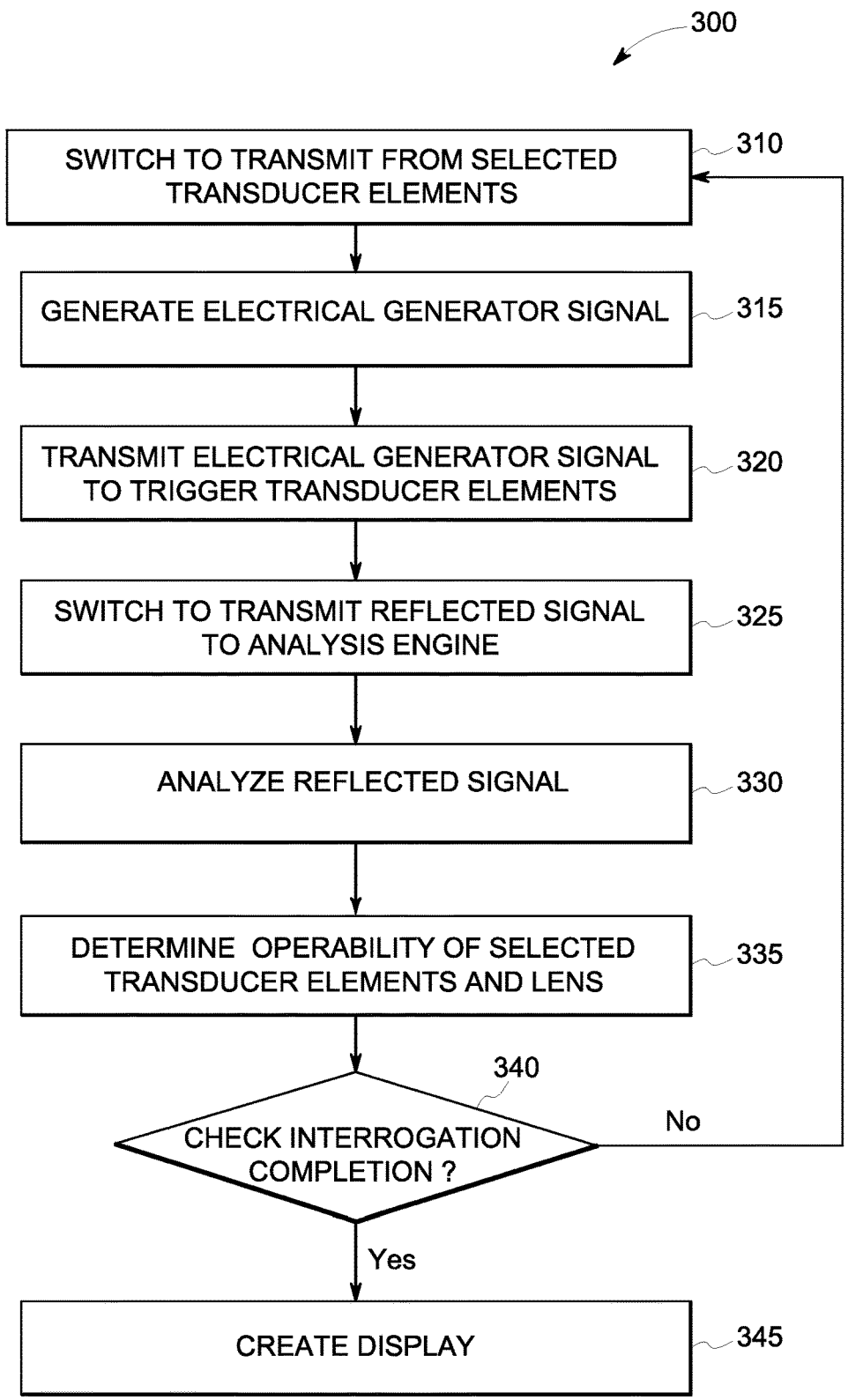
FIG. 2 shows a flow diagram illustrative of an example of a method of operating the system of FIG. 1 in accordance with the subject matter described herein.

For sake of example referring to FIG. 1, assume during testing, the acoustic probe 105 can be secured by the holder 215 for testing. Referring to FIG. 2, step 310 can include routing or switching the operative connection of the transceiver 130 to communicate with the selected transducer element(s) 110 of the acoustic probe 105 for testing. Step 315 can include instructing the electrical signal generator 180 to generate the electrical generator signal at the predefined frequency and amplitude. For example, the electrical generator signal 185 can be a voltage pulse. Step 320 can include routing or switching communication or transmission of the electrical generator signal to trigger the selected transducer elements 110 of the acoustic probe 105 being tested. In response and if operative or functional, the triggered selected transducer elements 110 can convert the electrical generator signal to an acoustic energy or radiation directed at the lens 108 of the acoustic probe 105. At least a portion of the acoustic energy or radiation will be deflected back toward the selected transducer element and re-converted back into a reflected electrical signal.

Step 325 can include routing or switching connection of the transceiver 130 so as to receive the reflected electrical signal from the selected transducer element of the acoustic probe. Step 330 can include analyzing or processing receipt of the reflected electrical signal from the selected transducer element. Step 340 can include determining an operability or functionality of the lens 108 and selected transducer element of the acoustic probe to convert between electrical and acoustic energy. If no reflected electrical signal is received at the transceiver 130, step 340 can include recording not to detect receipt of the electrical transducer signal 190 from the selected electrical transducer(s) elements 110 in response to the interrogation with the electrical generator signal in step 320. If the reflected electrical signal is detected and determined from analysis that the selected transducer element is operational or functional, step 340 can include recording that the selected transducer elements 110 is operative.

In cases where the transducer signal 190 is routed simultaneously from a subset group of the transducer elements 110, the subset group may correspond to a group of neighboring transducer elements 110. For example, absence or significant deviation of the amplitude of the electrical transducer signal in comparison to other electrical transducer signals 190 from other interrogated transducer elements 110 can be indicative of the inoperability or non-functionality (e.g., associated with cracking or other damage to the piezoelectric crystal) of the respective transducer element 110.

Step 350 can include determining or performing a check if an interrogation of all the transducer elements 110 of the acoustic probe 105 has been completed. If completed, step 355 can include providing a display (described below) including illustrations indicative of the recorded operability or functionality (e.g., pass versus fail, quantitative data) of the transducer elements 110 of the acoustic probe 105. If interrogation of certain transducer elements 110 has not been completed, step 350 can further include prompting the user to select another of the series of transducer elements 110 of the acoustic probe 105 for interrogation or testing or proceeding automatically, and returning to step 310 until all of the transducer elements 110 of the acoustic probe 105 are interrogated.

Figures 3, 4:
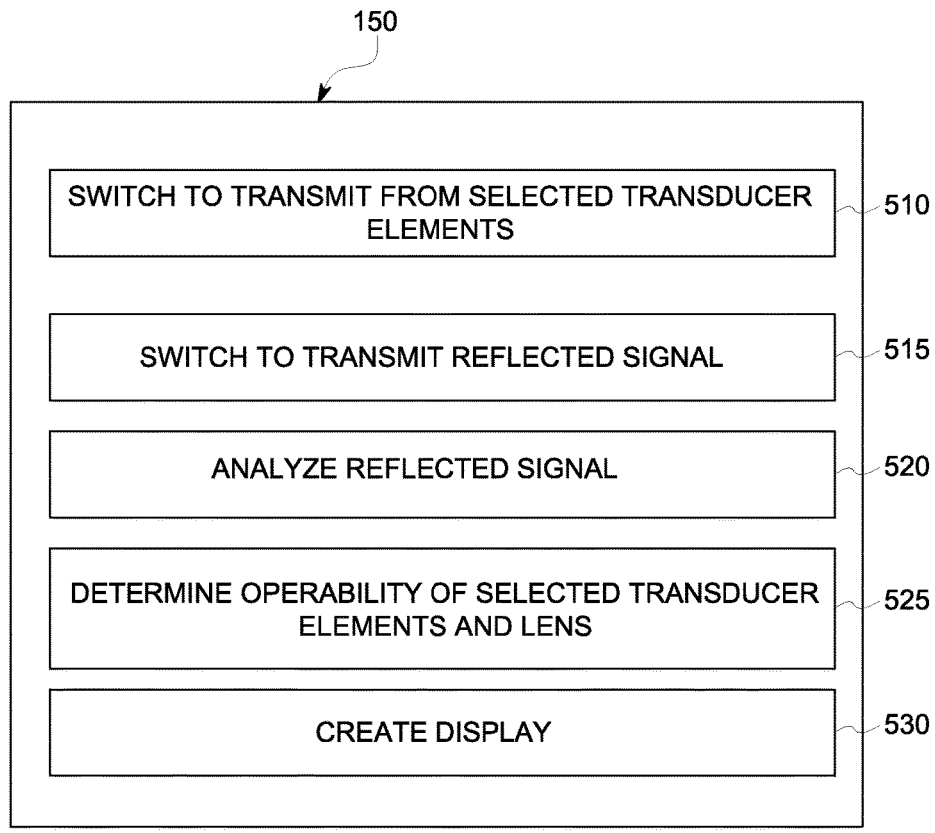
FIG. 3 shows schematic diagram illustrative of an example of a display generated by the system of FIG. 1 in accordance to the subject matter described herein.
FIG. 4 shows schematic diagram illustrative of an example of a computer program product of the system shown in FIG. 1 in accordance to the subject matter described herein.

FIG. 3 shows a schematic diagram of an example of a graphic display 400 in accordance to the subject matter described herein. The display 400 can provide illustrations indicative of an identifier 405 of the acoustic probe 105, a status of interrogation 410 of the transducer elements of the acoustic probe, a resultant responsive detection 415 of the reflected electrical signal from the selected transducer element, and an indication or status of operative ability or functionality 420 associated with the lens 108 and the identifiers 425 of each of the selected transducer element 110 of the acoustic probe 105 to convert between acoustic radiation and electrical signals in a required manner to perform imaging or other desired function.

FIG. 4 illustrates an example of the computer program product 150 for execution by the processor 145 to operate the system 100 in executing the method 300 described above. The computer program product 150 can include a first module 510 of program instructions for execution in operating the transducer element switch 170 to enable communication of the transceiver 130 with selected transducer elements 110 of the acoustic probe 105. A second module 515 can include program instructions for execution to in operating the transmit switch 175 between a first position to transmit the electrical generator signal 185 to the selected transducer elements 110 of the acoustic probe 105, and a second position to transmit the reflected electrical signal 190 from the selected transducer element 110 to the transceiver 130 for analysis. A third module 520 can include program instructions for execution in detecting and analyzing the reflected electrical signal 190 received from the selected transducer elements 110 of the acoustic probe 105. A fourth module 525 can include program instruction for execution in determining the operability or functionality of the selected transducer element 110, which can include comparing the reflected electrical signal 190 received from the selected transducer element 110 to another reflected electrical signal 190 received from another interrogated transducer element 110 of the acoustic probe 105. A fifth module 530 can include program instructions for creating the display 400 (See FIG. 3) illustrative of the operability or functionality (e.g., pass versus fail) of the selected transducer element 110 of the acoustic probe 105 for viewing by the user.

A technical effects of the subject matter described above can include, but is not limited to, providing the system 100 and method to test an operability of the acoustic probe 105 in a fast and yet repeatable manner. Another technical effect of the system 100 and method 300 is to provide for testing of the operability or functionality of the selected transducer elements 110 of the acoustic probe 105 without a need of certain cumbersome infrastructure (e.g., water tank, target, holder (optional)) that thereby reduces cost, provides increased mobility, and simplifies testing by the user.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. System for testing an acoustic probe having a lens in combination with a plurality of transducer elements adapted to convert between acoustic and electrical signals, the system comprising:
    a transceiver comprising:
        an electrical signal generator configured to generate an electrical generator signal;
        an element switch configured to selectively establish connection with at least one transducer element from the plurality of transducer elements of the acoustic probe;
        a transmit switch selectable between a first position and a second position, the first position to transmit the electrical generator signal from the transceiver to the acoustic probe, wherein the selected at least one transducer element of the acoustic probe converts the electrical generator signal into an acoustic signal that reflects off the lens of the acoustic probe and is then converted by the selected at least one transducer element of the acoustic probe into a reflected electrical signal, the second position to transmit the reflected electrical signal from the acoustic probe to the transceiver; and
        an analysis engine configured to receive the reflected electrical signal and determine operability of the lens and the selected at least one transducer element for acoustic and electrical conversion; and
    a display configured to provide an illustration indicative of the operative ability of the lens and the selected at least one transducer element of the acoustic probe for acoustic and electrical conversion.

2. The system of claim 1, further comprising:
    wherein the element switch comprises a relay matrix configured to establish connections in a sequential manner with the plurality of transducer elements of the acoustic probe.

3. The system of claim 1, wherein the element switch includes a switching integrated circuitry configured to establish the connection.

4. The system of claim 1, wherein the electrical signal generator is an alternating voltage source.

5. The system of claim 1, wherein the analysis engine compares the reflective electrical signal to at least one threshold to determine the operability of the lens and the selected at least one transducer element.

6. The system of claim 5, wherein the at least one threshold is an amplitude of another reflective electrical signal received from one of another of the transducer elements of the acoustic probe and transducer elements of another acoustic probe.

7. The system of claim 1, wherein in response to not detecting the reflected electrical signal from the selected at least one transducer element in response to transmission of the electrical generator signal to the acoustic probe, the display provides an illustration indicative of an inoperability of the lens and the selected at least one transducer element of the acoustic probe.

8. The system of claim 1, wherein in response to detecting the reflected electrical signal from the selected transducer element in response to communicating the electrical generator signal to the acoustic probe, the display provides an illustration indicative of an operability of the lens and the selected transducer element of the acoustic probe.

9. A method of testing an acoustic probe having a plurality of transducer elements adapted for conversion between acoustic and electrical signals, the method comprising:
    generating an electrical generator signal from an electrical signal generator;
    placing an transmit switch in a first position to transmit the electrical generator signal to the acoustic probe;
    selectively routing the electrical generator signal to at least one transducer element from the plurality of transducer elements of the acoustic probe via an element switch, wherein the selected at least one transducer element converts the electrical generator signal into an acoustic signal that reflects off a lens back toward the acoustic probe and is converted by the selected at least one transducer element into a reflected electrical signal;
    placing the transmit switch in a second position to transmit the reflected electrical signal from the acoustic probe;
    selectively routing the reflected electrical signal from the selected at least one transducer element via the element switch;
    detecting and analyzing the reflected electrical signal; and
    displaying an indication of the operative ability of the lens and the selected at least one transducer element of the acoustic probe for acoustic and electrical conversion.

10. The method of claim 9,
    wherein the element switch comprises a relay matrix to establish connections in a sequential manner with the plurality of transducer elements of the acoustic probe.

11. The method of claim 9, wherein the element switch comprises a switching integrated circuitry.

12. The method of claim 9, wherein in response to not detecting the reflected electrical signal from the selected at least one transducer element generated in response to communicating the acoustic signal to the acoustic probe, generating a display signal to trigger the illustration to indicate inoperability of the lens and the selected at least one transducer element of the acoustic probe.

13. The method of claim 9, wherein in response to detecting the reflected electrical signal generated in response to communicating the acoustic signal to the acoustic probe, generating a display signal to trigger the illustration to indicate the operability of the lens and the selected at least one transducer element of the acoustic probe.

14. The method of claim 9, further including comparing the reflected electrical transducer signal to at least one threshold to determine the operability of the lens and the selected at least one transducer element.

15. The method of claim 14, wherein the at least one threshold is an amplitude of another reflective electrical signal received from another of the transducer elements of the acoustic probe.

16. The method of claim 15, wherein comparing includes comparing a value of a parameter of the reflected electrical signal of the selected at least one transducer element of the acoustic probe to a value of the parameter for another of the plurality of transducer elements of the acoustic probe.

* * * * *